US009248148B2

(12) United States Patent
Stockham

(10) Patent No.: US 9,248,148 B2
(45) Date of Patent: Feb. 2, 2016

(54) MONO (IRON HYDROXYPYRONE) AND COMBINATION (IRON HYDROXYPYRONE AND GI INFLAMMATION INHIBITING AGENTS) COMPOSITIONS FOR ANAEMIA OR *H. PYLORI* INFECTIONS

(75) Inventor: Michael Arthur Stockham, Essex (GB)

(73) Assignee: Iron Therapeutics Holdings AG, Wollerau (CH)

( * ) Notice: Subject to any disclaimer, the term of this patent is extended or adjusted under 35 U.S.C. 154(b) by 684 days.

(21) Appl. No.: 12/992,528

(22) PCT Filed: May 14, 2009

(86) PCT No.: PCT/GB2009/001231
§ 371 (c)(1),
(2), (4) Date: Apr. 11, 2011

(87) PCT Pub. No.: WO2009/138761
PCT Pub. Date: Nov. 19, 2009

(65) Prior Publication Data
US 2011/0177172 A1 Jul. 21, 2011

(30) Foreign Application Priority Data
May 15, 2008 (GB) .................. 0808835.3

(51) Int. Cl.
*A01N 59/16* (2006.01)
*A61K 33/00* (2006.01)
*A61K 31/4439* (2006.01)
*A61K 33/26* (2006.01)

(52) U.S. Cl.
CPC ............. *A61K 33/00* (2013.01); *A61K 31/4439* (2013.01); *A61K 33/26* (2013.01)

(58) Field of Classification Search
CPC ... A61K 31/4439; A61K 33/00; A61K 33/26; A61K 2300/00
See application file for complete search history.

(56) References Cited

U.S. PATENT DOCUMENTS

| 4,834,983 | A | 5/1989 | Hider et al. |
| 5,177,068 | A | 1/1993 | Hider et al. |
| 2003/0069218 | A1 | 4/2003 | Stockham et al. |
| 2007/0161600 | A1 | 7/2007 | Helenek et al. |
| 2008/0193531 | A1* | 8/2008 | Hermelin et al. ............. 424/474 |

FOREIGN PATENT DOCUMENTS

| EP | 0107458 | 5/1984 |
| JP | 59-93071 | 5/1984 |
| JP | 2001-525848 | 12/2001 |
| WO | 9641627 | 12/1996 |
| WO | 9816218 | 4/1998 |
| WO | WO 98/16218 | * 4/1998 ............. A61K 31/28 |
| WO | 98/52547 | 11/1998 |
| WO | 0189534 | 11/2001 |
| WO | 02/24196 | * 3/2002 |
| WO | 0224196 | 3/2002 |
| WO | 03097627 | 11/2003 |
| WO | 2005048912 | 6/2005 |
| WO | 2007108712 | 9/2007 |

OTHER PUBLICATIONS

Sodium lauryl sulfate. at http://www.drugs.com/inactive/sodium-lauryl-sulfate-124.html 2000-2015.*
Lactose. at http://www.drugs.com/inactive/lactose-monohydrate-368.html 2000-2015.*
Singapore Written Opinion for Application No. 201008312-9; Filing Date May 14, 2009—date of mailing Oct. 11, 2011—6 pages.
Chinese First Office Action for Application No. 200980125291.4; Issuing Date Apr. 13, 2012—6 pages.
Chinese First Office Action for Application No. 200980125291.4 (English language translation); Issuing Date Apr. 13, 2012—6 pages.
Harvey et al., "Ferric trimaltol corrects iron deficiency anaemia in patients intolerant of iron," Aliment Pharmacol Ther, 1998, vol. 12, pp. 845-848.
Barrand et al., "Effects of the pyrones, maltol and ethyl maltol, on iron absorption from the rat small intestine," J Pharm. Pharmacol, 1987, vol. 39, pp. 203-211.
Barrand et al., "Dissociation of a ferric maltol complex and its subsequent metabolism during absorption across the small intestine of the rat," Br. J. Pharmacol, 1991, vol. 102, pp. 723-729.
Levey et al., "Characteristics of Iron(III) Uptake by Isolated Fragments of Rat Small Intestine in the Presence of the Hydroxypyrones, Maltol and Ethyl Maltol," Biochemical Pharmacology, 1998, vol. 37, No. 10, pp. 2051-2057.
Sarker et al., "Causal Relationship of *Helicobacter pylori* With Iron-Deficiency Anemia or Failure of Iron Supplementation in Children," Gastroenterology, Nov. 2008, vol. 135, No. 5, pp. 1534-1542.
Singh et al., "Lipid peroxidation effects of a novel iron compound, ferric maltol. A comparison with ferrous sulphate," J. Pharm. Pharmacol, 1990, vol. 42, pp. 276-279.
Intellectual Property Office—Search Report—date of search Aug. 14, 2007—Application No. GB0710144.7—2 pages.
Intellectual Property Office—Search Report—date of search Sep. 16, 2008—Application GB0808835.3—2 pages.
International Search Report —PCT/GB2009/001231—mailing date Oct. 5, 2009—6 pages.
IPRP—PCT/GB2009/001231—issuance of report Nov. 17, 2010—1 page.

(Continued)

*Primary Examiner* — Suzanne Ziska
(74) *Attorney, Agent, or Firm* — K&L Gates LLP

(57) ABSTRACT

There is provided a composition or kit of parts comprising: one or more compounds capable of treating and/or preventing an inflammatory disease of the gastrointestinal tract: and an iron hydroxypyrone, for increasing the level of iron in a patient's bloodstream and/or treating and/or preventing anaemia such as iron deficiency anaemia. A composition comprising iron hydroxypyrone is also provided for administration to a subject: having or at risk of having achlorhydria; wherein the gastric pH of the subject is equal to or greater than about 4; or wherein the subject has an inflammatory disease of the gastrointestinal tract.

20 Claims, No Drawings

(56) References Cited

OTHER PUBLICATIONS

Written Opinion of the International Searching Authority—PCT/GB2009/001231—11 pages.
Second Office Action for Chinese Application No. 200980125291t4, dated Mar. 4, 2013.
Written Opinion of the European Patent Office for European Application No. 09 746 078.6, dated Jun. 20, 2013.
Halter et al., "Long-term Effects of *Helicobacter pylori* Infection on Acid and Pepsin Secretion," Yale J. Biol. Med., 1996, vol. 69, No. 1, pp. 99-104.
First Examination Report on corresponding Australian patent application No. 2009247762 mailed Dec. 18, 2013.
Chinese Office Action for corresponding Chinese patent application No. 200980125291.4 issued Sep. 22, 2013.
Champagne, et al., "Low gastric hydrochloric acid secretion and mineral bioavailability," Adv Exp Med Biol., 1989, vol. 249, pp. 173-84, abstract (1 page).
C. Hutchinson, et al., "Proton pump inhibitors suppress absorption of dietary non-haem iron in hereditary haemochromatosis," Gut, 2007, vol. 56, pp. 1291-1295.
A. Jacobs, et al., "Role of gastric secretion in iron absorption," Gut, 1969, vol. 10, pp. 226-229.
L. Powell, et al., "Iron Absorption and Iron Overload," Clinics in Gastroenterology, vol. 10, No. 3, Sep. 1981, pp. 707-735.
E. Sarzynski, et al., "Association between proton pump inhibitor use and anemia: a retrospective cohort study," Dig. Dis. Sci., Aug. 2011, vol. 56, No. 8, pp. 2349-53, abstract (1 page).
Annibale et al., "Concomitant alterations in intragastric pH and ascorbic acid concentration in patients with *Helicobacter pylori* gastritis and associated iron deficiency anaemia," Gut, 2003, 52, pp. 496-501.
Jacobs et al., "Effect of gastric juice on iron absorption in patients with gastric atrophy," Gut, 1969, 10, pp. 488-490.
Jacobs et al., "Gastric Factors Influencing Iron Absorption in Anaemic Patients," Scandinavian Journal of Haematology, 1967, 4(2), pp. 105-110.
NISO Biomed document, "Pathological Conditions Related to Hypo- and Achlorhydria," no. date, 24 pages.
Skikne et al., "Role of Gastric Acid in Food Iron Absorption," Gastroenterology, 1981, 81, pp. 1068-1071.
Waxman et al., "Malabsorption of Hemoglobin Iron in Pernicious Anemia: Correction with Intrinsic Factor-Containing Substances," The Journal of Clinical Investigation, 1968, 47, pp. 1819-1825.
Windle et al., "Childhood *Helicobacter pylori* Infection and Growth Impairment in Developing Countries: A Vicious Cycle?" Pediatrics, 2007, 119(3), pp. e754-e759.
Kelsey et al., "Absorption of Low and Therapeutic Doses of Ferric Maltol, A Novel Ferric Iron Compound, in Iron Deficient Subjects Using a Single Dose Iron Absorption Test," Journal of Clinical Pharmacy and Therapeutics (1991) 15, 117-122.

\* cited by examiner

MONO (IRON HYDROXYPYRONE) AND COMBINATION (IRON HYDROXYPYRONE AND GI INFLAMMATION INHIBITING AGENTS) COMPOSITIONS FOR ANAEMIA OR *H. PYLORI* INFECTIONS

This invention relates to therapeutic compositions which comprise iron ions and to their medical applications.

An adequate supply of iron to the body is an essential requirement for tissue growth and the maintenance of good health in both man and animals. Moreover, in certain pathological conditions where there is an insidious blood loss, or where there is a mal-distribution of iron in the body, there may be a state of low iron stores in the body and a concomitant chronic anaemia. This is seen in inflammatory diseases of the gastrointestinal tract, such as gastric and peptic ulcers, reflux oesophagitis, ulcerative colitis and Crohn's disease.

Anaemia can also follow operations which result in serious blood loss and can be associated with gastrointestinal infections, such as those caused by *Helicobacter pylori*.

Achlorhydria (and hypochlorhydria) refer to states where the production of gastric acid in the stomach is absent or low, respectively. Achlorhydria can be due to many diverse causes including: pernicious anaemia, an autoimmune gastritis, other autoimmune conditions, such as autoimmune thyroid disease, any cause of severe chronic gastritis (*H. pylori* is the most common agent that may lead to the destruction of parietal cells (the cells that make hydrochloric acid) in the stomach, resulting in achlorhydria), mucolipidosis type IV (an autosomal recessive lysosomal storage disease), the use of antacids or drugs that decrease gastric acid production or transport, or atrophic gastritis.

The listing or discussion of an apparently prior-published document in this specification should not necessarily be taken as an acknowledgement that the document is part of the state of the art or is common general knowledge.

WO 96/41627 describes ferric iron complexes of hydroxypyrones, which comprise a carboxylic acid such as citric acid. The compositions are useful for the treatment of iron deficiency anaemia.

The use of certain metal ion complexes for treating gastrointestinal infection with *Helicobacter pylori* is disclosed in WO 98/16218. The complexes include complexes of iron in the ferric state. The patients were not, however, treated with acid reducing regimens.

WO 01/89534 describes the use of cobalt salts to selectively treat gastrointestinal infections caused by *H. pylori*.

WO 02/24196 discloses compositions in solid form, such as powders, comprising a mixture of a ferrous salt and a hydroxypyrone which may be used to increase the level of iron in a patient's bloodstream or to treat and/or prevent gastrointestinal infection.

WO 2005/048912 describes methods and compositions for the treatment of *helicobacter pylori*-associated disorders using endoperoxide bridge-containing compounds.

WO 03/097627 discloses a method of forming an iron hydroxypyrone.

US 2007/0161600 describes the treatment of iron related conditions with iron-carbohydrate complexes.

It is known that the absorption of iron is aided by the acid secretion of the stomach and that absorption is more readily affected when iron is in the ferrous state. It is also known that antacids may impair the absorption of iron by the formation of insoluble complexes (Martindale, page 1347, 32nd Edition, 1999). Research suggests that taking acid-reducing drugs can cause iron deficiency due to reduced absorption (Aymard et al, Med. Toxicol. Adverse Drug Exp. 1988, vol. 3, pp 430-448). Hence, a person skilled in the art would not have expected iron to be available for absorption in the stomach in the presence of acid reducing agents (www.numarkpharmacists.com/hn/Drug/Famotidine.html).

There are many medical conditions where the gastric environment is unfavourable for iron absorption yet iron absorption is required in order to address anaemia. For example, where gastritis and a high pH (such as above 6.5) prevails the absorption of iron may be too low to effectively treat anaemia. Furthermore, the treatment regimen for conditions, such as *Helicobacter* infection, typically involves the use of acid reducing agents. The present invention can be considered, at least in part, to relate to the unexpected finding that acid-reducing regimen, such as are required for the treatment of, for example, ulcers, gastritis and acid reflux, can be compatible with certain iron hydroxypyrones and that the iron may be absorbed effectively from the iron hydroxypyrones despite the use of an acid-reducing regimen.

The present invention aims to alleviate some of the problems of existing anaemia treatments.

According to the invention in a first aspect there is provided a composition comprising: one or more compounds capable of treating and/or preventing an inflammatory disease of the gastrointestinal tract; and an iron hydroxypyrone, for increasing the level of iron in a patient's bloodstream.

In another aspect there is provided a composition comprising: one or more compounds capable of treating and/or preventing an inflammatory disease of the gastrointestinal tract; and an iron hydroxypyrone, for preventing and/or treating anaemia such as iron-deficiency anaemia.

In a further aspect there is provided a composition or kit of parts for increasing the level of iron in a patient's bloodstream comprising: one or more compounds capable of treating and/or preventing an inflammatory disease of the gastrointestinal tract; and an iron hydroxypyrone, preferably wherein the iron hydroxypyrone comprises iron in the ferrous state.

In a still further aspect there is provided a composition or kit of parts for increasing the level of iron in a patient's bloodstream comprising one or more compounds capable of treating and/or preventing an inflammatory disease of the gastrointestinal tract and an iron hydroxypyrone preferably with the proviso that when iron is in the ferric state, the compound is not a cobalt salt. Preferably, the composition does not comprise an antibiotic.

In another aspect, there is provided a composition comprising an iron hydroxypyrone, for administration to a subject having, or at risk of having, achlorhydria.

In one aspect of the invention there is provided a composition comprising an iron hydroxypyrone, for administration to a subject, wherein the gastric pH of the subject is equal to or greater than about 4, such as greater than 5 or 6, for example about 6.5 or above.

In another aspect of the invention, there is provided a composition comprising an iron hydroxypyrone for administration to a subject, wherein the subject has, or is suffering from, an inflammatory disease of the gastrointestinal tract and preferably the gastric pH of the subject is equal to or greater than about 4, such as greater than 5 or 6, for example about 6.5 or above.

In one embodiment of the invention, the inflammatory disease of the gastrointestinal tract requires a stomach acid reducing treatment regimen as defined herein. However, the inflammatory disease may, in one embodiment, not require an acid reducing treatment regimen as defined herein.

The iron hydroxypyrone, the inflammatory disease and the gastric pH, and combinations thereof, in any of the above aspects is preferably as defined herein.

In one embodiment of the invention, the iron hydroxypyrone is administered alone, such as in the absence of other pharmaceutically active compounds, for example in the absence of one or more compounds capable of treating and/or preventing an inflammatory disease of the gastrointestinal tract.

In one embodiment of the invention, the composition and/or iron hydroxypyrone is for the absorption of iron, preferably following oral administration, for example into the blood and/or body of a subject.

Examples of an inflammatory disease of the gastrointestinal tract which preferably requires a stomach acid reducing treatment regimen include gastric or peptic ulcers, reflux, oesophagitis, ulcerative colitis, Crohn's disease, gastritis, Zollinger-Ellison syndrome or acid reflux.

In all aspects or embodiments of the invention, the one or more compounds capable of treating and/or preventing an inflammatory disease of the gastrointestinal tract which preferably requires a stomach acid reducing treatment regimen preferably comprise an acid reducing regimen. Acid reducing regimens are well known to a person skilled in the art. For example, the acid reducing regimen may comprise one or more compounds capable of treating and/or preventing inflammatory diseases of the gastrointestinal tract, such as, for example, gastric or peptic ulcers, reflux oesophagitis, ulcerative colitis, Crohn's disease, gastritis, Zollinger-Ellison syndrome or acid reflux.

In all aspects and embodiments of the invention, the peptic ulcer is preferably a gastric ulcer and the anaemia is preferably iron-deficiency anaemia. The anaemia is preferably associated with an inflammatory disease of the gastrointestinal tract as defined herein.

In one embodiment of the invention, the anaemia is caused by blood loss following an operation and/or is associated with a gastrointestinal infection, such as those caused by *Helicobacter pylori*.

The composition and/or kit of parts according to the invention is preferably for administration to a human.

The term "subject" as used herein preferably refers to a mammal, such as a human. The term "mammal" also includes veterinary animals such as for example, horses, cows, sheep and pigs, as well as pets such as, for example, dogs, cats and hamsters.

In one embodiment of the invention, the subject has been, will be, or is being administered an acid reducing regimen or one or more compounds capable of treating and/or preventing an inflammatory disease of the gastrointestinal tract, as defined herein.

In one embodiment of the invention, the one or more compounds capable of treating and/or preventing an inflammatory disease of the gastrointestinal tract comprise an acid reducing regimen. Surprisingly, it has been found that an iron hydroxypyrone according to the invention can be administered to patients in combination with acid reducing therapies for treating gastrointestinal conditions in which there is produced excess stomach acid. The iron hydroxypyrone can also be administered to patients generally having a high gastric pH, such as equal to or greater than about 4, such as greater than 5 or 6, for example about 6.5 or above, for example, from greater than 4 to 8, 4.5 to 7, 5 to 6.5 or 5.5 to 6.0, and be absorbed effectively. The high gastric pH may be, for example, as a result of achlorhydria, administration of an acid reducing regimen, such as defined herein, or an inflammatory disease of the gastrointestinal tract as defined herein, as well as combinations thereof. The administration of the iron hydroxypyrone may be for the absorption of iron, for example, following oral administration and/or may be used to maintain levels of iron in the body of a subject i.e. to provide or maintain normal, healthy or nutritional levels of iron.

According to the present invention, the iron hydroxypyrone may be administered at the same time, before or after the one or more compounds capable of treating and/or preventing an inflammatory disease of the gastrointestinal tract, or the acid reducing regimen. In one embodiment, the iron hydroxypyrone is administered at the same time or subsequent to the one or more compounds or the acid reducing regimen. For example, the iron hydroxypyrone may be administered from 1 minute to 2 hours after the compound, more preferably from 10 minutes to 1 hour after the compound, most preferably about 30 minutes after the administration of the compound.

In one embodiment of the invention, the composition, as defined in any of the aspects or embodiments herein, is for administration to a human or animal having or suffering from an inflammatory disease of the gastrointestinal tract which preferably requires a stomach acid reducing treatment regimen. For example, the human or animal may be suffering from a gastric or peptic ulcer, reflux oesophagitis, ulcerative colitis, Crohn's disease, gastritis, Zollinger-Ellison syndrome, acid reflux and/or a peptic ulcer and is in need of treatment therefor.

In a preferred embodiment of the invention, as defined herein, the composition is for administration to a human or animal having a gastrointestinal infection.

Although the gastrointestinal infection may be any infection, the gastrointestinal infection is preferably caused by *Helicobacter pylori*.

Suitable molar ratios of the one or more compounds, or acid reducing regimen, to the iron hydroxypyrone are from 100:1 to 1:100, preferably from 50:1 to 1:50, more preferably from 10:1 to 1:10, such as from 5:1 to 1:5, for example 2:1 to 1:2. Preferably the ratio of one or more compounds to iron hydroxypyrone is from 10:1 to 1:10 by weight.

The acid reducing regimen may be administered in accordance with the normal dosage ranges for human patients for therapeutic or preventative treatment. in one embodiment of the invention, the composition may be adapted for maintenance therapy, or the prevention of an inflammatory disease of the gastrointestinal tract, wherein the disease state is as defined in any of the embodiments herein. Thus, the composition may comprise lower doses of the compound and iron hydroxypyrone than are used for the initial treatment of an established disease.

In one embodiment of the invention, the composition comprises a maintenance dose of one or more compounds capable of treating and/or preventing an inflammatory disease of the gastrointestinal tract, or the acid reducing regimen and a nutritional dose of iron hydroxypyrone, as iron. For example, the daily dose of the compound may be less than 400 mg, for example, less than 300 mg, 200 mg or 100 mg. Typical daily maintenance doses of the compound (such as omeprazole, pantoprazole or ranitidine) may be from 5 to 140 mg daily, such as from 10 to 100 mg, preferably 20 to 50 mg, as one or more administrations.

Examples of suitable nutritional doses, preferably daily, of the iron hydroxypyrone include less than 40 or 60 mg as iron, such as from 5 to 20 mg, as iron, for example about 15 mg (as iron). The dosages may be administered for 1 to 4 weeks typically.

In a further embodiment of the invention, as defined herein, the one or more compounds capable of treating and/or preventing an inflammatory disease of the gastrointestinal tract comprise one or more acid reducing agents. The acid reducing agent may reduce the acid level directly i.e., by neutralisation of the acid, or indirectly, i.e., by inhibiting receptors which cause the secretion of excess acid or by treating the underlying disease state, for example.

Compositions for treating gastrointestinal conditions containing a metal salt, an antibiotic and a proton pump inhibitor, in so-called "triple therapy" methods are known. Antibiotics and proton pump inhibitors are suitable for use in the compositions of the present invention, as defined herein. Suitable antibiotics include, for example, amoxycillin, metronidazole, clarithromycin and mixtures thereof. Suitable proton pump inhibitors include lansoprazole, omeprazole, pantoprazole and rabeprazole for example. $H_2$ receptor antagonists, such as ranitidine, famotidine, nizatidine, cimetidine, for example, may also be used in the present invention. Omeprazole may be in the form of omeprazole magnesium or sodium. Ranitidine may be in the form of ranitidine bismuth citrate or ranitidine hydrochloride.

In any aspect or embodiment of the invention, the one or more compounds capable of treating and/or preventing an inflammatory disease of the gastrointestinal tract, or acid reducing agent, may be selected from a proton pump inhibitor, an $H_2$ receptor antagonist, or a substance capable of neutralising acids, such as, for example, an alkaline agent, or a combination thereof, as defined herein or a cobalt compound as defined herein. The term "substances capable of neutralising acids" is intended to include pharmaceutically acceptable bases. Suitable examples of bases include hydrogen carbonates (bicarbonates), hydroxides, oxides, or carbonates, which are commonly used in the treatment of acid reflux. Preferably, the bicarbonates, hydroxides, oxides or carbonates are in combination with a pharmaceutically acceptable cation, such as an alkali metal, for example, sodium or potassium, or alkaline earth metal, for example, magnesium, calcium or a transition metal, such as, for example, cobalt or a metal such as aluminium.

In one embodiment of the invention, as defined herein, the acid reducing agent is selected from: omeprazole, lansoprazole, pantoprazole, ranitidine, famotidine, nizatidine, cimetidine, sodium bicarbonate, potassium bicarbonate, calcium carbonate, aluminium hydroxide, magnesium carbonate, cobalt carbonate or a combination thereof.

In any aspects or embodiments of the invention, the composition may further comprise an antibiotic such as, for example, amoxycillin, metronidazole, clarithromycin and mixtures thereof.

In the embodiments or aspects of the invention, the one or more compounds capable of treating and/or preventing an inflammatory disease of the gastrointestinal tract preferably comprises or consists of a cobalt compound.

The cobalt compound may comprise a cobalt salt. Suitable examples of cobalt salts are defined in WO 01/89534, the teachings of which are incorporated herein by reference. The cobalt salt is preferably a cobalt (II) salt, since it is well-known that cobalt (II) salts are readily available unlike cobalt (III) salts, and because there is concern over the long term safety of cobalt (III) salts.

The cobalt salt must be capable of providing cobalt ions (in hydrated form) at the site of a gastrointestinal infection. It is preferred that the cobalt salt, such as cobalt (II), comprises an anion which does not complex too strongly with the cobalt ion. Preferably the anion is the anion of a strong acid (ie, having a pKa of less than about 3, 4, 5, or 6, for example less than 2) and/or is monovalent.

Suitable anions include chloride, gluconate, nitrate, sulphate, phosphate, carbonate, hydroxide, acetate and mixtures thereof (including salts containing two or more anions). Of these, chloride, carbonate, gluconate, hydroxide and acetate are more preferred.

The cobalt salts preferably contain cobalt ions in uncomplexed form (ie, such that $Co(H_2O)_6^{2+}$ ions are formed when the salt is in aqueous solution, for example) or in the form of complexes in which the cobalt ion is relatively weakly bound such that the complex at least partly dissociates to provide cobalt ions in a form suitable for uptake into *H. pylori* at the site of infection, for example.

Alternatively, the cobalt compound may comprise a cobalt complex. Suitable examples of ligands to form cobalt complexes are defined in WO 98/16218, the teachings of which are incorporated herein by reference. Preferred cobalt complexes include, for example, cobalt, preferably in the (II) or (III) state, complexed with ascorbate, aspartate, citrate, gluconate, histidine, malate, maltol, glutamate, glutamine, succinate, gluconate, or tartrate or combinations thereof.

In one embodiment of the invention, as defined herein, the cobalt compound comprises cobalt (II) gluconate or cobalt (II) chloride, preferably in their hydrated forms (i.e., the dihydrate for cobalt (II) gluconate or the hexahydrate for cobalt (II) chloride), or a combination thereof.

In one embodiment of the invention, the amount of cobalt compound is selected such that it is selective for the treatment of gastrointestinal infections caused by *Helicobacter pylori* i.e., it is present in an amount lower than the MIC for other microorganisms, particularly beneficial bacteria, in the intestinal tract.

The daily amount of cobalt compound, such as cobalt (II) gluconate or cobalt (II) chloride, is preferably less than 200 mg (as cobalt), such as less than 100 mg (as cobalt), for example from 2 to 50 mg, such as from 5 to 20 mg (as cobalt).

In one embodiment, the amount of compound (for example cobalt), such as a cobalt salt, which is required for the treatment of gastrointestinal conditions according to the invention varies from 1 to 50 mg of compound per day, more preferably 1 to 30 mg per day, such as 5 mg or 20 mg per day (preferably as cobalt), for example. A suitable dosage form comprises 10 mg of compound (preferably as cobalt) and such a dosage will typically be administered twice daily for several weeks (eg 1 to 4 weeks) in order to treat the infection. It will be appreciated by those skilled in the art that other dosage regimens may be equally applicable in the method of the invention. The cobalt compound may be in a slow release form as described in WO 01/89534, for example.

The term "iron hydroxypyrone" as used herein is intended to include compositions which comprise a hydroxypyrone and iron. The term includes, for example, complexes of iron with a hydroxypyrone, such as, for example, ferric trimaltol, as well as mixtures comprising an iron compound, such as a salt or a complex of iron, and a hydroxypyrone in a substantially non-complexed form (such as less than 10%, 5%, 2%, or 1% hydroxypyrone complexed), for example ferrous or ferric gluconate and maltol, preferably in the solid state.

The iron hydroxypyrone may suitably comprise iron in the ferrous ($Fe^{2+}$) or ferric ($Fe^{3+}$) oxidation states. Alternatively, the iron hydroxypyrone may comprise a mixture of iron in the ferrous and ferric oxidation states.

In one embodiment of the invention, the iron hydroxypyrone comprises iron in the ferric state. In an alternative embodiment, the iron hydroxypyrone comprises iron in the ferrous state, particularly where the iron hydroxypyrone is in the form of a solid, such as a powder or tablet.

The hydroxypyrone is preferably a 3-hydroxy-4-pyrone. Suitable pyrones include 3-hydroxy-4-pyrone itself or a 3-hydroxy-4-pyrone in which one or more of the hydrogen atoms attached to ring carbon atoms are replaced by an aliphatic hydrocarbon group of 1 to 6 carbon atoms, or a 5-hydroxy-pyrone, such as Kojic acid. The most preferred pyrones are maltol (3-hydroxy-2-methyl-4-pyrone) and ethylmaltol. The hydroxypyrone may, alternatively, be a natural product (such as meconic acid or iso-maltol) which may be converted to another hydroxypyrone in vivo.

Certain hydroxypyrones, such as maltol, are available commercially. With others, a convenient starting material in many instances consists of 3-hydroxy-4-pyrone which is readily obtainable by the decarboxylation of 2,6-dicarboxy-3-hydroxy-4-pyrone (meconic acid). For example, 3-hydroxy-4-pyrone may be reacted with an aldehyde to insert a 1-hydroxyalkyl group at the 2-position, which group may then be reduced to produce a 2-alkyl-3-hydroxy-4-pyrone. The preparation of 2-ethyl-3-hydroxy-4-pyrone, etc, by this route is described in the published U.S. application Ser. No. 310,141 (series of 1960). Other preparation methods are described by Spielman, Freifelder, J. Am. Chem. Soc. Vol 69 Page 2908 (1947).

It will be appreciated by a person skilled in the art that these are not the only routes available to these compounds and their iron complexes and that various alternatives may be used.

In one embodiment of the invention, the iron hydroxypyrone is a ferric complex with hydroxypyrone. It is preferred that the ferric complex is a 1:3 molar complex of iron to the hydroxypyrone.

Preferably, the iron hydroxypyrone is a ferric maltol, a ferric ethylmaltol or mixtures thereof. It is particularly preferred that the ferric maltol is ferric trimaltol. The ferric trimaltol may be prepared according to any method known in the art. Preferably, the ferric trimaltol is prepared as set out in WO 03/097627, the teachings of which are incorporated herein by reference.

In another embodiment of the invention, the iron hydroxypyrone is in the form of a solid, a liquid or a suspension in a liquid and comprises a mixture of a ferrous or a ferric salt and a hydroxpyrone as defined herein. The solid mixture may also be dry (i.e, substantially free of liquid such as water i.e., the mixture comprises less than 10 wt. %, 5 wt. % or 2 wt. %, such as less than 1 wt. % liquid). Solid mixtures of ferrous salts and hydroxypyrones are stable on storage for a moderate period of time under substantially dry conditions. However, on dissolution in water, the compositions undergo a reaction in which some or all of the ferrous iron is oxidised to ferric iron.

The ferrous or ferric salt can be an iron (II) or iron (III) salt with any pharmaceutically acceptable anion. Preferably, the iron (II) salt is iron (II) carbonate or an iron (II) carboxylate.

The ferrous or ferric salt is preferably an iron (II) or iron (III) carboxylate. The iron (II) carboxylate may be selected from, for example, iron (II) gluconate, iron (II) succinate or iron (II) fumarate and mixtures thereof. The iron (III) carboxylate is preferably selected from ferric citrate, ferric ammonium citrate or ferric tartrate and mixtures thereof.

In any aspect or embodiment of the invention, the compound (or acid reducing regimen) preferably comprises a cobalt compound, such as, for example, cobalt (II) gluconate or cobalt (II) chloride, preferably in a daily dosage of, for example, less than 100 mg (as cobalt), and the iron hydroxypyrone comprises, in a solid form, a mixture of a ferrous or ferric salt of a carboxylic acid and a hydroxypyrone, such as maltol or ethylmaltol, preferably in a daily dosage in terms of iron content of, for example, 15 to 50 mg (as iron). In any embodiment of the invention, the daily dosage of the compound is preferably a maintenance dosage and the daily dosage of the iron hydroxypyrone is preferably nutritional (i.e., it can maintain the levels of iron stored in the body by, for example, replacing any iron "leakage").

The composition or kit of parts for increasing the level of iron in a patient's bloodstream and/or treating and/or preventing anaemia according to the invention may comprise any of the compounds or iron hydroxypyrones set out above, or combinations thereof.

In particular, the kit of parts may comprise the one or more compounds capable of treating and/or preventing an inflammatory disease of the gastrointestinal tract, or acid reducing agent, such as one or more compounds capable of treating gastritis, acid reflux and/or a peptic ulcer, and an iron hydroxypyrone, wherein the compounds and the iron hydroxypyrone are packaged separately and optionally instructions are provided for the administration of the two separate parts. This may be appropriate where there is otherwise a storage incompatibility between the compound and iron hydroxypyrone.

In one embodiment, the composition comprises a co-formulation (for example, in the same solid or liquid) of the one or more compounds capable of treating and/or preventing an inflammatory disease of the gastrointestinal tract, or acid reducing agent such as, for example, one or more compounds capable of treating gastritis, acid reflux and/or a peptic ulcer, as defined herein, and an iron hydroxypyrone, as defined herein. This may be suitable where there is no storage incompatibility between the compound and the hydroxypyrone.

In a preferred composition or kit of parts of the invention, the iron hydroxypyrone comprises a solid or dry (i.e., substantially free of liquid such as water i.e., the liquid comprises less than 10 wt. %, 5 wt. % or 2 wt. %, such as less than 1 wt. %) mixture of a ferrous carboxylate, such as gluconate, and maltol or ethyl maltol and the one or more compounds capable of treating and/or preventing an inflammatory disease of the gastrointestinal tract or acid reducing agent comprises a cobalt compound, such as cobalt gluconate (preferably cobalt(II) and hydrated). The molar ratio of ferrous salt to maltol or ethylmaltol is preferably about 1:3.

In an alternative preferred composition or kit of parts of the invention, the iron hydroxypyrone comprises ferric trimaltol and the one or more compounds capable of treating and/or preventing an inflammatory disease of the gastrointestinal tract or acid reducing agent, such as one or more compounds capable of treating gastritis, acid reflux and/or a peptic ulcer, comprises potassium bicarbonate. The potassium bicarbonate may be present in the solid or liquid state, such as an aqueous solution.

Conveniently, the composition of the invention is in the form of a powder (which term covers fine powders and granulates) comprising a mixture of the powdered iron hydroxypyrone and the one or more compounds. The iron hydroxypyrone may be in crystalline form, in amorphous form or in other solid forms but is preferably crystalline. The ferrous or ferric salt may contain water of crystallisation i.e., it may be in the form of a hydrate.

In a further aspect, the compositions of the invention are used in medicine and, in another aspect, pharmaceutical compositions are provided which comprise the composition of the invention together with a pharmaceutically acceptable diluent or carrier.

A method of forming a composition according to the invention is also provided which comprises mixing the one or more compounds capable of treating and/or preventing an inflammatory disease of the gastrointestinal tract, or acid reducing agent, and an iron hydroxypyrone, all as defined herein. The mixing may take place in the solid or liquid state. For example, both components may be in the form of substantially dry solid such as powders, or tablets, preferably having a moisture or water content less than 10 wt. %, 5 wt. %, 2 wt. % or 1wt. %.

In the above aspects and embodiments of the invention, the pharmaceutical composition or kit of parts of the invention may be adapted for oral administration. Suitable forms for oral administration include powders, tablets and capsules (such as gelatin capsules) as well as solutions or suspensions in aqueous or non-aqueous liquids, oil-in-water liquid emulsions, or water-in-oil liquid emulsions.

Suitable pharmaceutically acceptable diluents and carriers include, for example, lubricants such as magnesium stearate, stabilising and suspending agents such as methylcellulose and povidone and other tableting agents and dose bulking agents such as lactose and flow aids such as Aerosil 2000™. Particularly useful diluents and carriers are wetting agents or surfactants, preferably nonionic or ionic surfactants. Examples of suitable nonionic surfactants include polyoxyl 10 oleyl ether and polysorbates. An example of a suitable ionic surfactant is sodium lauryl sulphate.

Alternatively, the pharmaceutical composition may be provided as a liquid or a suspension in liquid form, as a powder for reconstitution prior to oral or parental administration or it may be formulated for use as a suppository. Liquids carriers are preferably sterile and pyrogen-free: examples are saline and water. Liquid formulations are particularly suitable for oral and parenteral administration.

More than one iron hydroxypyrone or one or more compounds capable of treating and/or preventing an inflammatory disease of the gastrointestinal tract or acid reducing agent of the invention may be contained in the pharmaceutical composition of the invention, and other active compounds may also be included. Typical possible additives include, for example, flavourings and colourings known to a person skilled in the art, as well as those set out herein.

The pharmaceutical compositions of the invention may be formulated in unit dosage form ie, in the form of discrete portions containing a unit dose, or a multiple or sub-unit dose. Preferably, the compositions of the invention are formulated to give a rapid release of the iron for optimal absorption in the body.

Whilst the dosage of the composition given in each particular case will depend upon various factors, including the particular components of the composition, it may be stated by way of guidance that maintenance at a satisfactory level of the amount of iron present in the human (or animal) body will often be achieved using a daily dosage, in terms of the iron content of the compound, which lies in a range from about 1 to 150 mg, such as from 10 to 120 mg (preferably as iron). However, it may be appropriate in certain cases to give daily dosages either below or above these levels. Compositions containing 15 to 50 mg iron, to be taken once daily, twice daily or three times daily (depending on the severity of the anaemia) are, for example, suitable for the treatment of anaemia.

The compositions of the invention suitably contain from 0.1% to 20% by weight iron, such as 0.1% to 10% by weight, for example, preferably 2 to 10% by weight.

In one embodiment of the invention, there is provided a composition comprising: an iron hydroxypyrone; and optionally one or more compounds capable of treating and/or preventing an inflammatory disease of the gastrointestinal tract which preferably requires a stomach acid reducing treatment regimen, for administration to a subject having, or at risk of having, achlorhydria.

The composition is preferably for increasing the level of iron in a patient's bloodstream and/or for preventing and/or treating anaemia such as iron deficiency anaemia as described above.

The achlorhydria may be a result of any of the causes set out above or known to a person skilled in the art, such as, for example, pernicious anaemia, an autoimmune gastritis, other autoimmune conditions, such as autoimmune thyroid disease, any cause of severe chronic gastritis (*H. pylori* is the most common agent that may lead to the destruction of parietal cells (the cells that make hydrochloric acid) in the stomach, resulting in achlorhydria), mucolipidosis type IV (an autosomal recessive lysosomal storage disease), the use of antacids or drugs that decrease gastric acid production or transport, for example one or more compounds capable of treating and/or preventing an inflammatory disease of the gastrointestinal tract which requires a stomach acid reducing treatment regimen as defined herein, or atrophic gastritis.

In one embodiment of the invention the achlorhydria is associated with, or caused by, an inflammatory disease of the gastrointestinal tract such as, for example, a gastric or peptic ulcer, reflux oesophagitis, ulcerative colitis, Crohn's disease, gastritis, Zollinger-Ellison syndrome, acid reflux and/or a peptic ulcer.

In another embodiment of the invention, the achlorhydria is associated with, or caused by, atrophic gastritis or a gastrointestinal infection, such as caused by *Helicobacter pylori*.

The composition for administration to a subject having, or at risk of having, achlorhydria, may be as defined in any of the aspects or embodiments herein, in particular, the compound and the iron hydroxypyrone may be as defined in any of the above embodiments.

In one embodiment of the invention, the subject may have detectable antibodies against the $H^+/K^+$ ATP-ase proton pump and/or the gastric pH may remain high (such as greater than 4.0, 5.0, 6.0 or 6.5), despite stimulus, such as maximum pentagastrin stimulation and/or high gastrin levels may be detected and/or a maximal acid output of less than 6.9 m/mole/h, such as less than 5.0 m/mole/h.

In any of the above aspects or embodiments of the invention, the pH of the environment where iron is absorbed, such as the gastric environment or gastrointestinal tract, for example, the gastric pH, is preferably equal to or greater than about 4, such as greater than 5 or 6, for example about 6.5 or above, for iron absorption, for example, from 4 to 8, 4.5 to 7, 5 to 6.5 or 5.5 to 6.0. Thus, the one or more compounds or acid reducing regimen in any aspect or embodiment may also be defined as adapted to increase, or capable of increasing, the pH of the environment for iron absorption, such as the gastric environment or gastrointestinal tract, for example, the gastric pH, to greater than about 4, such as greater than 5 or 6, for example about 6.5 or above (for example from for example, from 4 to 8, 4.5 to 7, 5 to 6.5 or 5.5 to 6.0, 5 to 8, preferably 6 to 7), for or before iron absorption.

The following non-limiting examples illustrate the invention and do not limit its scope in any way. In the examples and throughout this specification, all percentages, parts and ratios are by weight unless indicated otherwise.

EXAMPLES

Example 1

Patient 1

The patient had been taking Gaviscon™ which contains potassium bicarbonate as an acid reducer to reduce acid reflux. The patient had a gall bladder rupture requiring surgery and became very anaemic due to blood loss. He continued to take Gaviscon™ but was also given ferrous sulphate tablets for his anaemia. He had serious side effects of gastric intolerance and severe headaches and the ferrous sulphate failed to correct his anaemia. He commenced treatment using maltol and ferrous gluconate, whilst continuing Gaviscon™ and his anaemia was corrected (haemoglobin rose from 8.8 g % to 11.8 g %) after a month. At a dose of 45 mg/day his iron was well tolerated.

Example 2

Patient 2

On a long term basis this patient takes Losec™, omeprazole, a proton pump inhibitor of gastric acid secretion. He had a hip replacement operation where a significant amount of blood was lost causing iron deficiency anaemia. His anaemia was not corrected (Hb>11.0g %) until a course of maltol and ferrous gluconate at 15 mg daily was undertaken. He continues to use maltol and ferrous gluconate as a "boost" when feeling tired as his haemoglobin levels are always on the low side of normal.

Example 3

The following is an example of a pharmaceutical composition according to the invention, which is suitable for formulation into gelatin capsules:

| Component | Amount (mg) |
| --- | --- |
| Ferrous gluconate | 240 |
| Maltol | 200 |
| Cobalt gluconate | 100 |
| Carrier (lactose) | balance to fill capsule |

Example 4

Method

Thirteen normal female volunteers were treated such that their gastric pH was adjusted to >6.5 with 0.5M sodium bicarbonate solution (acid reducing regimen). Using a Heidelberg capsule the maltol iron formulation was given orally and the % of the dose absorbed into the blood and the whole body determined.

Results

Absorption of iron from the 10 mg dose of the maltol iron formulation was 10.72%. For the 20 mg dose the maltol iron formulation gave 8.00%.

This is a level of absorption that would be expected with normal volunteers with a standard iron preparation, such as ferrous sulphate, at normal gastric pH.

Conclusions of Studies

In the study involving 13 female subjects the maltol iron formulation was given along with sodium bicarbonate (acid reducing regimen) and the gastric pH was in excess of 6.5. Surprisingly, there was no inhibition of absorption at this higher pH. The presence of the maltol makes the formulation suitable for special medical conditions with gastritis and higher pH values associated with iron deficiency anaemia.

Discussion

The work shows that iron hydroxpyrones according to the invention are well absorbed at a high pH (greater than 6.5). Surprisingly, the iron hydroxypyrones can therefore deliver iron in a high pH environment, for example the presence of an acid reducing regimen such as used for the treatment of *Helicobacter* infection. Thus, there is an unexpected advantage to use an iron preparation containing a hydroxypyrone such as maltol since a high pH, such as caused by the presence of the acid reducing regimen does not alter the solubility or bioavailability of the iron, which would have been expected. Other work has shown that cobalt at low doses can have beneficial activity in the treatment of *Helicobacter* infection. In the light of these results a co-formulation of cobalt with iron products containing maltol would be particularly useful for treating the anaemia arising with the *Helicobacter* infection.

The invention claimed is:

1. A method for increasing the level of iron in a subject's bloodstream and/or for preventing and/or treating anaemia in the subject, wherein the method consists of the steps of administering a composition comprising an iron hydroxypyrone to the subject, and maintaining the gastric pH of the subject greater that 4 during said method.

2. The method according to claim 1, wherein the composition is administered by oral administration or, wherein the method is for the absorption of iron.

3. The method according to claim 1, wherein the anaemia is iron deficiency anaemia.

4. The method according to claim 1, wherein the gastric pH is greater than 5 or 6.

5. The method according to claim 4, wherein the gastric pH is about 6.5 or above.

6. The method according to claim 1, wherein the iron hydroxypyrone comprises a ferric complex with hydroxypyrone, or a mixture of a ferrous or ferric salt and a hydroxypyrone and wherein the hydroxypyrone comprises a 3-hydroxy-4-pyrone or a 3-hydroxy-4-pyrone in which one or more of the hydrogen atoms attached to the ring carbon atoms are replaced by an aliphatic hydrocarbon group of 1 to 6 carbon atoms.

7. The method according to claim 1, wherein the iron hydroxypyrone comprises ferric trimaltol or an iron (II) or iron (III) carboxylate and maltol.

8. The method according to claim 1, wherein the composition is administered to a human or animal.

9. A method for increasing the level of iron in a subject's bloodstream and/or for preventing and/or treating anaemia in the subject, wherein the method consists of the step of administering a composition comprising an iron hydroxypyrone to the subject having, or at risk of having, achlorhydria, and wherein the iron hydroxypyrone is administered in the absence of a gastrointestinal pH lowering agent.

10. The method according to claim 9, wherein the anaemia is iron deficiency anaemia.

11. The method according to claim 9, wherein the achlorhydria is associated with an inflammatory disease of the gastrointestinal tract or wherein the achlorhydria is associated with atrophic gastritis or a gastrointestinal infection, such as caused by *Helicobacter pylori*.

12. A method for increasing the level of iron in a subject's bloodstream and/or for preventing and/or treating anaemia in the subject, wherein the method consists of the step of administering a composition comprising an iron hydroxypyrone to a subject, and maintaining the gastric pH of the subject greater than 4 during the method, wherein the subject has an inflammatory disease of the gastrointestinal tract.

13. The method according to claim 12, wherein the anaemia is iron deficiency anaemia.

14. The method of claim 12, wherein the gastric pH of the subject is greater than 5 or 6.

15. The method according to claim 14, wherein the gastric pH is about 6.5 or above.

16. The method according to claim 6, wherein the ferrous salt is an iron (II) carboxylate.

17. The method according to claim 6, wherein the iron (II) carboxylate is selected from iron (II) gluconate, iron (II) succinate and iron (II) fumarate.

18. The method according to claim 1, claim 9 or claim 12, wherein the pH of the environment where iron is absorbed is greater than 4.

19. A method for increasing the level of iron in a subject's bloodstream and/or preventing and/or treating anaemia in the subject, wherein the method comprises the step of administering a composition comprising ferric trimaltol to the subject, wherein the gastric pH of the subject is greater than 6 and wherein iron is absorbed in the subject from the ferric trimaltol.

20. The method according to claim 1, claim 9 or claim 12, wherein the iron hydroxypyrone is administered with a pharmaceutically acceptable diluent or carrier.

* * * * *